US00PP37436P3

(12) United States Plant Patent
Bull

(10) Patent No.: US PP37,436 P3
(45) Date of Patent: May 19, 2026

(54) ***RUDBECKIA* PLANT NAMED 'BullRudihir 123'**

(50) Latin Name: *Rudbeckia hirta L.*
Varietal Denomination: BullRudihir 123

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 0 days.

(21) Appl. No.: 19/235,317

(22) Filed: Jun. 11, 2025

(65) Prior Publication Data

US 2026/0107860 P1 Apr. 16, 2026

Related U.S. Application Data

(60) Provisional application No. 63/731,838, filed on Jun. 12, 2024.

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell
(74) *Attorney, Agent, or Firm* — The Webb Law Firm

(57) ABSTRACT

A new and distinct variety of *Rudbeckia* plant having a compact growth habit and large, peach-cherry bicolored blooms.

1 Drawing Sheet

Botanical classification: *Rudbeckia hirta* L.
Varietal denomination: 'BullRudihir 123'.

BACKGROUND OF THE INVENTION

The present invention comprises a new and distinct cultivar of *Rudbeckia* plant known by the varietal name 'BullRudihir 123'. The new variety was discovered in August of 2022 in Gönnebeck, Germany as the result of a planned breeding program with the purposes of providing *Rudbeckia* plants with improved growth, more uniformity, a compact growth habit, increased branching, attractive foliage, large blooms, and unique flower colors. The new variety is the result of a cross between an unpatented *Rudbeckia hirta* L. variety having an internal breeder's reference of "BR02-2021" (female parent) and an unpatented *Rudbeckia hirta* L. variety having an internal breeder's reference of "BR8-2021" (male parent) from the breeder's own collection. The new variety was first asexually reproduced via in-vitro tissue culture cuttings in Gönnebeck, Germany in September of 2022. The new variety is similar to its parental varieties in botanical classification, but exhibits bicolor (peach-cherry) flowers, earlier blooming, increased branching, and more attractive foliage with smaller leaves than the parental varieties. Further, its compact growth habit distinguishes 'BullRudihir 123' from its parent varieties.

When 'BullRudihir 123' is compared to *Rudbeckia hirta* L. variety named 'Cherokee Sunset Mix' (unpatented), 'BullRudihir 123' is similar to 'Cherokee Sunset Mix' in botanical classification, but 'BullRudihir 123' exhibits a different flower color (cherry-peach bicolor), flowers, improved plant quality, more uniform growth with increased self-branching, and more attractive foliage, that distinguish it from 'Cherokee Sunset Mix'. Further, the following characteristics distinguish 'BullRudihir 123' when generally compared to other *Rudbeckia* varieties known to the breeder:

Large, bicolored cherry-peach blooms with a brown center;
Good self-branching;
A medium, compact, and uniform growth habit;
Healthy, green foliage;
Long bloom time;
Uniformity in the crop; and
Unique flower color combination.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWINGS

The accompanying photographic drawing illustrates the new variety at 19 weeks of age, with the color being as nearly true as is possible with color illustrations of this type:

FIG. 1 shows an entire plant of the new variety.

DESCRIPTION OF THE PLANT

The following detailed description sets forth the characteristics of the new variety as the result of asexual reproductions performed via in vitro tissue culture cuttings carried out in Gönnebeck, Germany. Plants of the new variety were grown outdoors in 21 cm (4 liter) pots under normal field production conditions, and the color readings and measurements were observed outdoors under natural light on 19-week-old plants in Gönnebeck, Germany. Color references are primarily to The 2015 R.H.S. Colour Chart of The Royal Horticultural Society of London, Sixth Edition, except where terms of ordinary significance are used.

PLANT

Time to initiate roots: About 7-10 days at approximately 18° C.
Time to develop roots: About 35-38 days at approximately 16-18° C.
Time to produce a finished flowering plant from a rooted cutting: About 11-12 weeks in a 21 cm container.
Rooting habit: Exhibits numerous roots of medium thickness that are freely branching and healthy in appearance.
Plant height: 40.0-55.0 cm.
Plant width: 35.0-40.0 cm.
Vigor: Medium.
Disease/pest resistance: Nothing unusual noted to date.
Temperature tolerance: From −3 to +40° C.
Drought tolerance: Relative Tolerance.
Branching habit: Exhibits one dominant strong branch with several lateral side branches. The lateral branches are upright, forming an attractive habit.
Branches (flowering stems):
*Number per plant.*—25-35.
*Length.*—10.0-32.0 cm.
*Diameter.*—5.0-10.0 mm.
*Internode length.*—3.0-10.0 cm.
*Angle.*—Upright and outward.
*Strength.*—Strong.
*Texture.*—Pubescent.
*Color.*—Green (Close to 144A to 144B).
Foliage:
*Arrangement.*—Single.
*Leaf.*—Length: 4.0-21.0 cm. Width: 1.5-7.0 cm. Shape: Oblanceolate. Apex: Acuminate. Base: Attenuate to acute. Margin: Dentate and undulate. Texture: Upper surface: Rough, haired. Lower surface: Rough, haired. Color: Young leaves: Upper surface: Medium green (close to 137B). Lower surface: Medium green (close to 137C). Mature leaves: Upper surface: Medium green (close to 137B to 137C). Lower surface: Medium green (close to 137D). Petiole: None present. Veins: Venation type: Pinnate. Color: Upper surface: Light green (close to 145C). Lower surface: Light green (close to 145A).

INFLORESCENCE

Bud:
*Diameter.*—1.5-3.8 cm.
*Length.*—1.8-3.8 cm.
*Color.*—Green (close to 145B) when closed with a brown middle (close to 187A) when open.
Appearance: Elliptic-shaped ray florets and tubular-shaped disc florets.
Natural flowering season: Flowering occurs from June-October in Gönnebeck, Germany, beginning approximately 11-12 weeks after planting.
Average number of inflorescences per plant: 18-32.
Average number of inflorescences per branch: 1-3.
Disc and ray floret arrangement: Single composite flower with many whorls.
Fragrance: None present.
Inflorescence:
*Diameter.*—7.0-12.0 cm.
*Height (depth).*—2.0-4.0 cm.
*Diameter of disc.*—2.0-4.0 cm.
*Receptacle height.*—1.0-1.5 cm.
*Receptacle diameter.*—3.0-5.5 cm.
Ray florets:
*Number per inflorescence.*—45 to 60.
*Arrangement.*—Many whorls.
*Length.*—2.0-6.0 cm.
*Width.*—1.0-1.8 cm.
*Shape.*—Elliptical.
*Apex.*—Emarginate.
*Base.*—Acute.
*Margin.*—Entire.
*Texture.*—Upper surface: Smooth and glabrous. Lower surface: Rough.
*Color.*—When opening: Upper surface: Peach (close to 26B) with a Cherry (close to 183A) middle. Lower surface: Close to 162B. At maturity: Upper surface: Mostly cherry (close to 64A). Lower surface: Closer to 16A. Ground color description: Peach (close to 26B) to mostly cherry (close to 64A).
*Venation.*—Appearance: Parallel. Color: Upper surface: Same color as the florets. Lower surface: Same color as the florets.
Disc florets:
*Number per inflorescence.*—Numerous; 400 to 500.
*Arrangement.*—In the center of receptacle.
*Length.*—5.0-8.0 mm.
*Width.*—About 1.0 mm.
*Shape.*—Tubular.
*Apex.*—Five-pointed.
*Color.*—Immature: Brown (close to 200A). At maturity: Brown (close to 200A).
Phyllaries:
*Number per inflorescence.*—23-30.
*Arrangement.*—In three whorls.
*Length.*—1.0-3.2 cm.
*Width.*—3.0-8.0 mm.
*Shape.*—Lanceolate.
*Apex.*—Elongated oval.
*Base.*—Fused.
*Margin.*—Undulate.
*Texture.*—Upper surface: Rough, with pubescence present. Lower surface: Rough, with pubescence present.
*Color.*—Immature: Upper surface: Green (close to 138A). Lower surface: Green (close to 138B). At maturity: Upper surface: Green (close to 138A). Lower surface: Green (close to 138B).
Reproductive organs:
Androecium:
*Presence.*—On disc florets.
*Number (per floret).*—Numerous.
*Filament length.*—1.0-2.0 mm.
*Filament color.*—Brown (close to 200A).
*Anther.*—Shape: Oval. Length: 1.0 mm. Color: Brown (close to 200A).
*Pollen.*—Color: Yellow (close to 17A). Amount: Plentiful-too much to quantify.

Gynoecium:

*Presence*.—On disc and ray florets.

*Pistil length*.—About 2.0 mm.

*Stigma*.—Shape: Two-parted. Color: Brown (close to 200A).

*Style*.—Length: 1.0-2.0 mm. Color: Brown (close to 200A).

Seeds:

*Overall size*.—Approximately 2.0 mm.

*Color*.—Black (close to 202A).

I claim:

1. A new and distinct variety of *Rudbeckia* plant named 'BullRudihir 123', as is herein illustrated and described.

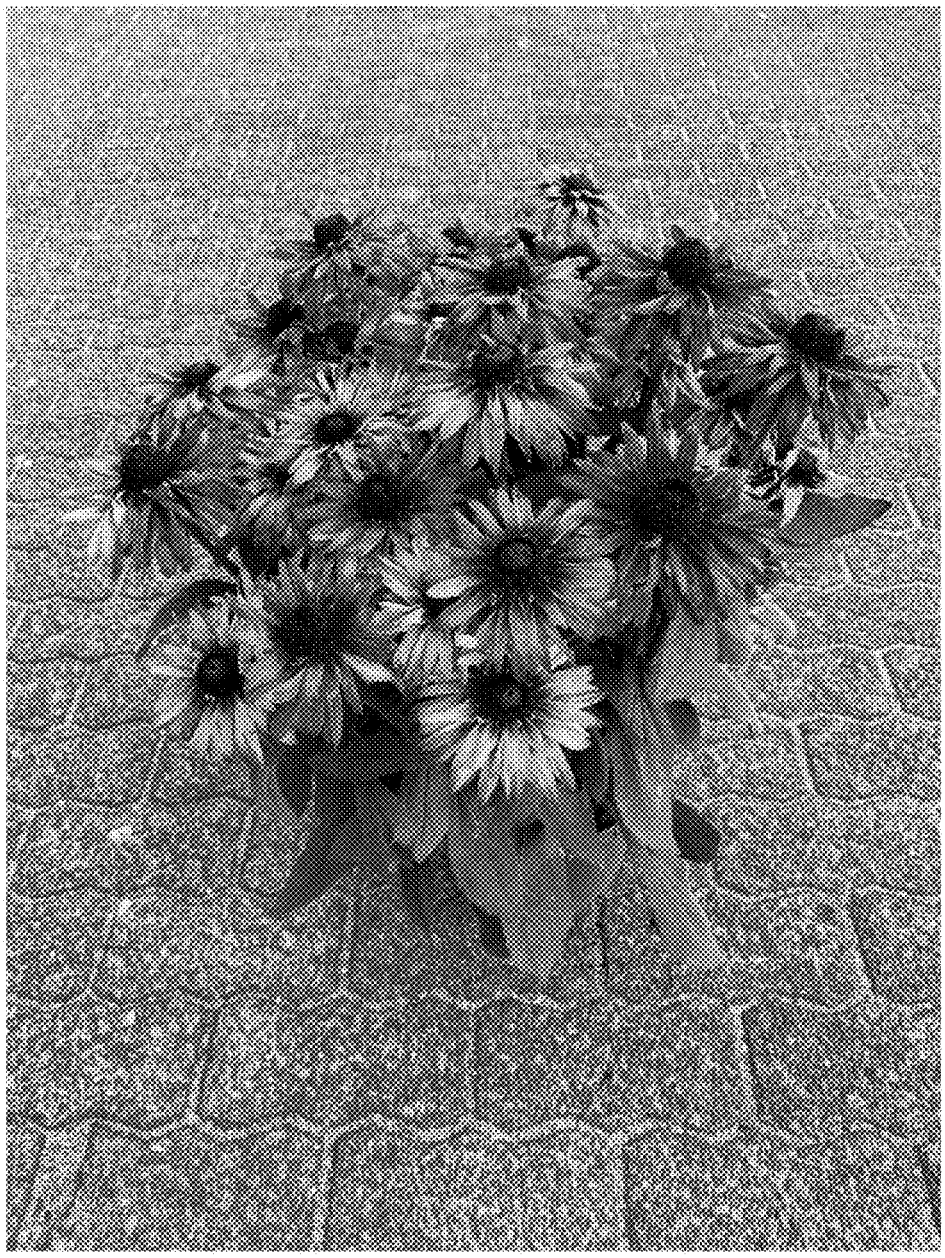

* * * * *